United States Patent
Stutz et al.

(10) Patent No.: US 8,206,721 B2
(45) Date of Patent: Jun. 26, 2012

(54) USE OF AN EXTRACT FROM SNOW ALGAE IN COSMETIC OR DERMATOLOGICAL FORMULATIONS

(75) Inventors: Cornelia Schürch Stutz, Staufen (CH); Daniel Schmid, Brugg (CH); Fred Zülli, Küttigen (CH)

(73) Assignee: Mibelle AG, Buchs (CH)

( * ) Notice: Subject to any disclaimer, the term of this patent is extended or adjusted under 35 U.S.C. 154(b) by 16 days.

(21) Appl. No.: 12/760,173

(22) Filed: Apr. 14, 2010

(65) Prior Publication Data

US 2010/0316720 A1   Dec. 16, 2010

(30) Foreign Application Priority Data

Jun. 12, 2009   (CH) ..................................... 0917/09

(51) Int. Cl.
*A61K 36/02* (2006.01)
(52) U.S. Cl. ................................ 424/195.17
(58) Field of Classification Search .................. None
See application file for complete search history.

(56) References Cited

U.S. PATENT DOCUMENTS

2008/0175805 A1* 7/2008 Schlemer .................. 424/63
2009/0142370 A1   6/2009 Shih et al.

FOREIGN PATENT DOCUMENTS

| DE | 10055558 A1 | 6/2002 |
|----|-------------|--------|
| FR | 2728467 A1  | 6/1996 |
| JP | 2002114703 A1 | 4/2002 |
| JP | 2004238519 A1 | 8/2004 |
| WO | 0024369 A1  | 4/2000 |

OTHER PUBLICATIONS antiagingandskincare.com. Retrieved from the internet. <http://www.agingandantiagingskincare.com/causes-of-skin-aging.htm>. Retrieved on Oct. 29, 2011. 2 pages.*
ebooks. Retrieved from the internet. <http://ebookslink.com/what-is-aging-anti-aging-tips/what-is-aging-anti-aging-tips/>. Retrieved on Oct. 29, 2011. 3 pages.*
CCCryo.com. Retrieved from the internet. <http://cccryo.fraunhofer.de/web/infos/welcome>. Retrieved on Oct. 29, 2011. 1 page document and 14 page document.*
Leya et al. Response of arctic snowand permafrost algae to high light and nitrogen stress by changes in pigment compositionand applied aspects for biotechnology. FEMS Microbiol Ecol. Jan. 2009. 67. pp. 432-443.*
Duddone et al. DNA Macroarray Study of Skin Aging-related Genes Expression Modulation by Antioxidant Plant Extracts on A Replicative Senescence Model of Human Dermal Fibroblasts. Phytotherapy Research. 25. 2011. pp. 686-693.*
Seki et al. Effects of astaxanthin from *Haematococcus pluvialis* on human skin. Fragrance Journal. 12. 98-103.*
pharmainfo.net. <ttp://www.pharmainfo.net/pharma-student-magazine/nanoemulsions-0>. Retrieved from the internet. Retrieved on Oct. 28, 2011. 12 pages.*
ezinearticles. Retrieved from the internet. <http://ezinearticles.com/?How-to-Treat-Aging-Skin-Caused-by-UV-Rays-of-the-Sun&id=4399820>. Retrieved on Oct. 29, 2011. 2 pages.*
Odeberrg et al. Oral bioavailability of the antioxidant astaxanthin in humans is enhanced by incorporation of lipid based formulations. European Journal of Pharmaceutical Sciences. 19. 2003. pp. 299-304.*
Bark et al. The benefits of Astaxanthin on skin and collagen. Jan. 12, 2010. 1 page.*
Suganuma et al. Astaxanthin attentuates the UVA-induced up-regulation of matrix metalloproteinase-1 and skin fibroblast elastase in human dermal fibroblasts. Journal of Dermatological Science. vol. 58, issue 2, May 2010. pp. 136-142 (10 pages).*
ehow.com. Astaxanthin. Retrieved from the internet. <http://www.ehow.com/about_5595083_foods-containing-astaxanthin.html>. Retrieved on Oct. 28, 2011. 3 pages.*
Search report for priority application CH00917/09, dated Aug. 28, 2009.

* cited by examiner

*Primary Examiner* — Melenie McCormick
(74) *Attorney, Agent, or Firm* — Maginot, Moore & Beck, LLP

(57) ABSTRACT

The present invention relates to the use of an extract from snow algae, especially an extract from *Chlamydocapsa* sp (snow algae) in cosmetic and/or pharmaceutical products. More particularly, the invention relates to *Chlamydocapsa* sp. (snow algae) in cosmetic and/or pharmaceutical products employed to guard against extrinsic aging of the skin caused by negative environmental exposure, for instance, UV radiation or air pollution, but also to guard against intrinsic aging of the skin as influenced by aging-specific gene expression levels. The invention relates furthermore to a method for producing extracts from snow algae, suitable for topic applications.

13 Claims, No Drawings

USE OF AN EXTRACT FROM SNOW ALGAE IN COSMETIC OR DERMATOLOGICAL FORMULATIONS

BACKGROUND

The present invention relates to the use of an extract from snow algae, especially an extract from *Chlamydocapsa* sp (snow algae) in cosmetic and/or pharmaceutical products. More particularly, the invention relates to *Chlamydocapsa* sp. (snow algae) in cosmetic and/or pharmaceutical products employed to guard against extrinsic aging of the skin caused by negative environmental exposure, for instance, UV radiation or air pollution, but also to guard against intrinsic aging of the skin as influenced by aging-specific gene expression levels. The invention relates furthermore to a method for producing extracts from snow algae, suitable for topic applications.

The skin acts as a barrier keeping the body safe from dehydration whilst guarding against harm due to chemical and mechanical environmental exposure. Denoted especially harmful to the skin is the UV radiation of sunlight. The skin, like every other tissue, is subject to aging processes. Aging of the skin is termed either intrinsic or extrinsic. Intrinsic aging is a chronological genetically determinate process whereas extrinsic aging is governed by outer factors, smoking and excessive exposure to the sun being deemed especially harmful. These extrinsic factors result in what is called premature aging of the skin.

Aging of the skin is not just a problem cosmetically. Aged skin goes hand-in-hand with a reduced barrier function and thus diminished protection from environmental exposure. This prompts a fatal progression, accelerating aging of the skin even more.

Aged skin is characterized by a reduction in cell regeneration in the epidermis and a drop in the production of collagen structural proteins in the dermis. The skin becomes less elastic and its water content is reduced.

There already exists a variety of cosmetic and dermatological formulations for the treatment of skin aging, the active ingredient used in the main in dermatological products being retinoic acid, whilst in cosmetic products, use is made of, in addition to UV filters, especially antioxidants such as vitamin C or vitamin E.

Plant, algae or fungous extracts rich in natural antioxidants also already find application as active ingredients in cosmetic formulations. Substances especially promising and attractive in this respect are plants or microorganisms exposed to extreme outdoor conditions, organisms thriving in a desert, polar or hot springs environment counting to be extremophilic because they needed to develop special adaptation techniques for their survival in these extreme habitats.

One special species of extremophils are snow algae which biologically count as cryoflora.

Algae are eukaryotic, plant-like organisms living in water capable of photosynthesis but which do not actually count as plants. Snow algae belong to the green algae, they being classified systematically as Chlorophyceae, Division Chlorophyta.

These are microscopic fresh water algae found in the eternal snow and glacier surfaces of polar and alpine regions of the earth (Arctic, Antarctic, Alaska, Greenland, West and East Coast of North America, Himalaya, Japan, New Guinea, Europe, Switzerland, China, Patagonias, Chile and South Orkney Islands). Their natural habitat is governed by extremely low temperatures, high UV radiation and nutrient deficiency to which they have become optimally adapted. They live in a unique microhabitat, namely the free water between the crystals in the snow. They color the massive snow surfaces in polar and alpine regions green and a brilliant red (blood snow e.g. *Chlamydomonas nivalis*) attributed to the spores of the algae. This red coloration of the spores serves as a UV screen achieved by the inclusion of carotenoids (astaxanthin).

At this time roughly 350 strains of snow algae are known, the most common being *Chlamydomonos nivalis*. Classifying snow algae phylogenetically is difficult, their systematics being in constant change. Many of the 350 strains stem from wild collections and characterizing algae taxonomically is still anything but complete genetically. The largest collection of snow algae (CCCryo, Culuture Collection of Cyrophilic Algae) is to be found in the Fraunhofer Institute for Biomedical Engineering (IMBT) in Berlin.

Also from an ecological point of view snow algae are becoming increasingly of interest by being able to absorb atmospheric $CO_2$ in thus influencing the greenhouse effect. They also serve as bioindicators, for example, for UV radiation directly involving a reduction in the ozone layer, or the acid-tolerant strains as indicators of acid rain.

Snow algae are collected generally in polar regions, cultivated and taxonomically determined as to the DNA level—see a German paper by Leya T, (2004): "Feldstudien and genetische Untersuchungen zur Kyrophilie der Schneealgen Norwestspitzbergens" concerning testing the cyrophilic reponse of snow algae in the northwest region of Spitzbergen, as published by Shaker Verlag, Aachen. Snow algae nowadays can be durably cultured in corresponding reactors, the temperature management of which together with the correct supply of air and light poses difficulties in culturing. Particularly the temperature requires special attention since growth of snow algae as a cryoflora is an optimum at around 12° C. The normal life-cycle of snow algae begins with germination in Spring when the slow melt of the snow and when sufficient water and nutrients are available. The green algae perform with the aid of chloroplasts photosynthesis and multiply until a relimitation of the nutrients triggers sporulation. Sporulation commences by the algae producing and incorporating carotenoides which protect the spores from UV radiation, resulting in the red algae spores causing the typical red coloration of the snow.

Currently, snow algae research is focussed on isolating various secondary metabolites from the snow algae such as, for example, carotenoides (xanthin, astaxanthin, etc.), cryoactive enzymes/proteins (cryoprotectors, for example) or antioxidants, such as described, for instance, in the paper by Bohne, F. & Linden H (2002): Regulation of cartenoid biosynthesis genes in response to light in *Chlamydomonas reinhardtii*. Biochim. Biophys. Acta 1579:26-34, Duval B., Shetty K. & Thomas W H (2000): Phenolic compounds and antioxidant properties in the snow alga *Chamydomonas nivalis* after expose to light, J. Appl. Phycol. 11: 559-566, Fábregas J., Otero A., Mased A. & Dominguez A. (2001): Two-stage cultures for the production of astxanthin from *Haemotococcus pluvalis*, J. Biotechnol. 89: 65-71.

Thus, US 2004/225167A1 describes a method for the production of carotenoids, zeaxanthin from green chlorphyta algae, it more particularly describing a method by which a carotenoid in a detergent-insoluble agent is produced. WO 2008/141757 or EP 995 325 A1 likewise describe a method for producing astaxanthin from *Haematococcus pluvialis* with which the carotenoid can be made in large quantities. To date no industrial application of the constituents of snow algae is known.

Continually cultivating snow algae, upgrading the biomass and isolating the cellular components still present a particular major challenge. Cultivating snow algae and isolating individual secondary metabolites are described, for example, in KR 20000072316 A or JP 0908772. Whilst US 2008/254056 A1 describes cultivating green algae of the species *Haematococcus pluvialis* and isolating astaxanthin. Here again, application of the extracts is restricted to the isolated substances such as astaxanthin or lutein.

In addition to the above, substances extracted or isolated from organisms exposed to extreme UV stress or water stress (dryness; freezing) likewise already find application as active ingredients in anti-aging cosmetics, examples of such active ingredients being ectoin and extracts with mycosporine-like amino acids (MAA). Ectoin is a low-molecular protecting agent belonging to the group of osmolytes or compatible solutes, it being produced by halophilic bacteria that live in salt flats. Ectoin protects the cells from heat and drought. DE 199 11 775 A1 describes the use of ectoin in cosmetic formulations for main cell DNA guarding against UV radiation and other DNA-detrimental factors, whilst DE 100 55 558 A1 describes skin care cosmetic preparations containing an extract of the green alga *Prasiola crispa antarctica* at home in the Antarctic and which produces UV-absorbing substances (mycosporine-like amino acids).

SUMMARY

One object of the present invention is to provide a cosmetic and/or pharmaceutical product for protection, treatment and care of the skin. More particularly the object is to provide a cosmetic and/or pharmaceutical product to prevent or delay skin aging with which both intrinsic as well as extrinsic skin aging can be treated.

This object is achieved in accordance with the invention by an extract from snow algae, more particularly from *Chlamydocapsa* sp. contained in a cosmetic and/or pharmaceutical product, said extract being produced by a reproducible method employing 2-phase cryoculturing.

It was found that with the extract as used in accordance with the invention (produced for example from *Chlamydocapsa* sp. (snow algae)), the hydrophilic and lipophilic cell constituents as well as the cytosols which are liposomal encapsulated and provided as powder have a positive effect on several parameters involved in skin aging. In particular, the extract protects against extrinsic factors which accelerate the process of skin aging especially due to oxidative reactions (photoaging, for example) whilst simultaneously acting likewise to protect against intrinsic skin aging caused by a change in the gene expression in aged skin. This combined protective effect is a novel approach for an holistic anti-aging treatment in cosmetics.

DETAILED DESCRIPTION

One method for producing a snow algae extract used in accordance with the invention is characterized by the steps:

culturing snow algae for example the strain *Chlamydocapsa* sp (CCCryo 101-99, IBMT strain collection, deposited with the Culture Collection of Algae and Protozoa with the Scottish Marine Institue, OBAN, Argyll PA 37 1QA, United Kingdom, submitted on Feb. 10, 2012, and given accession number CCAP 9/3) in a tube reactor system in 2-phase culturing, harvesting being done in the $2^{nd}$ phase (red phase);

producing an extract by solubilization of the cultured cells by means of high-pressure homogenization before extracting the constituents and stabilizing them with empty liposomes to obtain finely dispersed liposomes containing fat and water soluble cell fractions; and coating a matrix material with the basic extract and drying it by means of fluidized bed drying.

The following describes how the cosmetic and/or pharmaceutical formulation containing the snow algae extract by the method as described above is effective.

1. Protection against Intrinsic Skin Aging

The extract was tested on aging skin cell models based on human fibroblasts. In the first model aged fibroblast cells (naturally aged; after many divisions) were compared to young cells.

In the other model, fibroblast cells were prematurely aged by treatment with $H_2O_2$. To validate the models the expression of marker genes involved in the skin aging was analyzed. An anti-aging effect is verified when a substance can neutralize a gene being over or under expressed due to aging. Investigating the naturally aged fibroblast cells as detailled investigated in the following example 8 showed that an extract of snow algae stimulated the expression of the genes for type I and III collagens. Type I and III collagens are the main structure proteins in skin, i.e. aged skin is characterized by a reduced content of these collagen proteins. The same test also indicated a strong stimulation in the expression of the Klotho gene. The Klotho protein acts as a coreceptor of receptors of fibroblast growth factors such as insulin and IGF-1. Defects in the Klotho gene lead to a phenotype of premature aging. Klotho overexpression proved to lengthen the life span of mice. Correspondingly in the test as described here, the expression of Klotho in untreated aged cells as compared to young cells was reduced. By treating the aged cells with snow algae extract thus reduction could not only be neutralized but even overcompensated. In the test with the prematurely aged fibroblasts, as described further on in example 9, an example of snow algae proved to inhibit the expression of the genes for the matrix metalloproteinases 1 and 3, both of which exist in higher concentrations in aged skin and are responsible for the depletion of the structure proteins collagen and elastin in thus playing a central role in skin aging. This overexpression of the matrix metalloproteinases due to aging was neutralized by treatment with the snow algae extract.

2. Protection against Extrinsic Skin Aging

The effectiveness described in this case in vivo was confirmed in a trial on 20 candidates as detailled in example 10. A cream containing 3% by weight snow algae as the active ingredient was tested on the face in a half-side application. The test product was applied twice daily on 18 women and 2 men over a 3 week period. The placebo product was applied in each case to the other half of the face. All candidates spent the $2^{nd}$ week skiing during which the face was exposed to extreme environmental cold, dryness and high UV radiation. The results showed that the face half treated with the snow algae active ingredient was better protected against transepidermal water loss (TEWL) than the placebo side. The markedness of the face wrinkles was documented before and after treatment by means of a VisioFace® apparatus enabling high-resolution digital images to be taken of the whole face under controlled conditions. These images made at different times were compared by a software with the result that a significant reduction in wrinkles was found after treatment with the snow algae cream, whereas at the placebo side no significant change was apparent.

Producing suitable snow algae extracts comprises the following main steps:

a) mass culturing the cells in a tube reactor system and b) producing a total extract by means of high-pressure homogenization in making use of empty liposomes with
c) simultaneous application and drying of the extract on a suitable matrix material by means of fluidized bed drying.

Mass culturing the cells (step a) according to the records was implemented at a pH of 5.5 and temperature ranging from 4° C. to 15° C.

Expediently, step b) can be followed by
solubilizing the cells by high-pressure homogenization;
extracting and stabilizing ingredients with liposomes;
Both of these actions are implemented simultaneously in a single step in the method.

3. Producing the Biomass

To produce the snow algae extract of this invention firstly biomass is produced by culturing snow algae of the *Chamydocapsa* strain in the specific cultivar 101-99 (CCCryo 101-99 strain collection IBMT). Producing the biomass in a suitable tube reactor system under specific culturing conditions is done by known methods. Culturing is implemented in two phases as is detailled in example 1. The $1^{st}$ growth phase is followed by a $2^{nd}$ phase induced by a limited supply of nutrients, causing the snow algae to transform from the vegetative green phase into the stationary red phase as is characterized by the production of secondary metabolites such as, for example, various carotinoides.

On completion of culturing the biomass is separated from the culturing medium, and stored in deep-freeze at −20° C. until its further use.

4. Upgrading the Biomass

In the method as described for producing the cosmetic active ingredient from the snow algae biomass a variety of additives may be included, such as, for example, preservatives, antioxidants, pH stabilizers, fragrances or further substances as are useful in the preparation or in the cosmetic product.

The preservative may be any preservative of a natural or synthetic origin such as, for example, phenoxyethanol, benzoic acid, propionic acid, alcohol or silver chloride used as approved for cosmetics.

To additionally protect the extract from oxidation antioxidants such as, for example, ascorbic acid or tocopherol may be added.

When all components have been added, the mixture needs to be stirred to blend in the preservative along with other additives. For this purpose a paddle agitator, a homogenizer rod or pumping through static blenders may be employed.

Subsequent high-pressure homogenization as detailed in example 2 has two objectives:
disrupting the cell membranes so that the extractable substances are released, and
generating finely dispersed liposomes containing the fat and water soluble fractions of the cells.

Suitable high-pressure homogenizers are marketed commercially available. The principle of the reaction chamber has to be selected from a multitude of possibilities and tested prior to being adapted. Likewise needing to be tested is the number of cycles through the reaction chamber until all cell walls are solubilized or the wanted homogenity of the extract is achieved.

The resulting extract can then be directly worked into a cosmetic product such as, for example, creams, soaps, lotions, gels or hair serums or made into a, physically, highly stable powder with a long shelf life by means of fluidized bed drying. Fluidized bed drying has the advantage of making the full surface of each and every particle available in the flying phase of drying, the continual thorough agitation resulting in a homogenous product temperature with uniform drying as is highly effective, time-saving and gentle to the starting product. Temperature and air flow in the method has to be adapted and optimized in each case to the starting products and the wanted properties of the final product as a granulate, pellet, powder or other as is detailed in example 3.

Likewise possible is to provide topic preparations with the snow algae extract in accordance with the invention. The active ingredient in such compositions is finely distributed and thus has preference in being applied to the skin in a form as is resorbed by the skin, especially gels, emulsions or microemulsions being suitable in this respect.

If the extract is intended to serve as a semi-finished product a thickener may be added which can be any natural or synthetic thickener allowed for cosmetics, such as, for example, xanthan gum, hyaluronic acid, carrageen, dextrin, modified starch or agar.

A preferred inventive snow algae extract in accordance with the invention contains in a cosmetic and/or pharmaceutical composition 0.01 to 10.0 weight % of a snow algae *Chlamydocapsa* sp (CCCryo 101-99, IBMT strain collection) by solubilizing the cultured cells by means of high-pressure homogenization before extracting the constituents and stabilizing them with empty liposomes to obtain finely dispersed liposomes containing the fat and water soluble cell fractions.

Also included in addition to these components are pharmaceutical and cosmetic compatible additives such as thickeners, antioxidants, pH stabilizers and the like, preferably (b) 0.01 to 5 weight % thickeners
(c) 0.001 to 1 weight % antioxidants
(d) 0.001 to 2 weight % pH stabilizers
(e) 0.001 to 2 weight % additives are used.

EXAMPLES

Example 1

Producing the Biomass

Producing the biomass was done in close cooperation with the IBMT Fraunhofer Institute in Berlin in two phases. During the first phase in production the snow algae were nurtured in a corresponding culturing medium (3N-BBM) with a pH of 5.5 and cultured at a temperature ranging from 4° C. to 15° C. with a supply of $CO_2$. The time for the algae to double was approx. 1.3 days at a temperature of 14.5° C. On completion of the first production phase the snow algae were transferred to a nutriant-limited culturing medium to induce the transition into the red/stationary phase. Culturing in the $2^{nd}$ phase of production was implemented with the same parameters as for the $1^{st}$ phase. On completition of the $2^{nd}$ phase the cell biomass was separated from the culturing medium and frozen at −20° C.

Example 2

Producing a Lipsomal Extract

The frozen biomass was thawed and then blended with a preservative and a dispersion containing empty liposomes in a size of approx. 50 nm. The concentration of the snow algae biomass in the blend may range from 0.01 g/l to 10 g/l. The blend was then subjected to high-pressure homogenization four times at a pressure of 1200 bar ($1.2 \times 10^8$ N m$^{-2}$) to solubilize the cell walls of the snow algae(i.e. lyse), releasing the fat and water soluble components of the cytosol and simultaneously encapsulating the result in the form of a liquid nanoemulsion. The extract produced in this way contains dispersed and emulgated cell fractions. With this technology the insoluble lipid particles from cell fractions and the cytosol can be made bio-available.

Example 3

Drying the Extract by Means of Fluidized Bed Drying

The snow algae extract as produced and upgraded above can be blended in differing ratios with a matrix material, it being ideally blended in the ratio 1/1 with isomalt/PVP, although other ratios, for example, 1/2, 1/5 or 1/10 are possible. Suitable matrix materials are, for example, maltose, maltodextin, microcrystalline cellulose, silificized microcrystalline cellulose, povidon or other sugar derivatives, also in combination with cellulose. The thus prepared extract was then dried by means of fluidized bed drying at a spraying rate of 50 to 60 g/min and an average temperature of max. 50° C. down to a residual moisture content of approx. 5%. Managing the temperature and degree of dryness can be tweaked according to the wanted granulate size and bulk density of the final product.

Unless stated otherwise, the percentages of the employed components given in the following examples 4 to 7 relate to the total amount (w/w).

Example 4

Anti-Photoaging Cream with Snow Algae Extract

TABLE 1

| Phase | Components | % w/w |
|---|---|---|
| A | water | ad 100 |
|  | di-sodium EDTA | 0.1 |
|  | methylpropandiol | 2.0 |
| B | cetyl alcohol and glycerol stearate and PEG-75 stearate and Ceteth-20 and steareth-20 | 4.0 |
|  | sodium-acrylate copolymer and hydrogenized polyisobutene and phospholipid and Polyglycerol-10-stearate and *helianthus annuus* (sunflower) seed oil | 1.0 |
|  | stearyl alcohol | 1.5 |
|  | $C_{12-15}$ alkyl benzoate | 4.0 |
|  | 4-hydroxy benzoic acid ester in phenoxy ethanol | 0.7 |
| C | cyclopenta siloxane and dimethicone cross polymer | 3.0 |
|  | cyclotetra siloxane and cyclopenta siloxane | 4.0 |
| D | snow algae extract | 2.0 |
| E | perfume | 0.1 |

The components as listed above in Table 1 were processed into an anti-photoaging cream as described in the following:

Both phase A and phase B components were blended and heated to 75° C., after which phase B was added to phase A and stirred until blended homogenously. This was followed by 5 minutes of homogenization before the resulting mass was stirred cooled to 40° C. The phase C components were then premixed and added to the above blend, followed by adding the components of phases D and E in the blend, the resulting mass of which was homogenized and subsequently stirred until having cooled down to room temperature.

The pH should range from 5.5 to 6.0. Otherwise is should be adjusted by the addition of sodium hydroxide solution or citric acid.

Example 5

Cell-Protecting Serum with Snow Algae Extract

TABLE 2

| Phase | Components | % w/w |
|---|---|---|
| A | octanic acid/decanic acid triglycerides | 10.0 |
|  | glycerine-(and) saccharaose-laurate (and) saccharaose-dilaurate (and) saccharaose trilaurate (and) sorbitol | 2.0 |
|  | perfume | 0.12 |
| (A/C) | dehydroacetic acid (and) benzyl alcohol (and) water | 0.7 |
| B | glycerine | 15.0 |
|  | sodium polyacrylate | 0.7 |
| C | water | ad 100 |
|  | pentylene glycol | 5.0 |
|  | lactic acid 80% | 0.145 |
| D | snow algae extract | 5.0 |
| E | silicium dioxide dimethyl silylate | 0.1 |

The components as listed above in Table 2 were processed into an cell-protecting serum as described in the following:

The components of phase C were blended with one half of the preservative (dehydroacetic acid and benzyl alcohol). The components of phase B were blended and added to phase C. Then the components of phase A were blended and followed by the addition of the remaining preservative. After stirred addition of phase A, the snow algae extract was added to the mixture. To finish with, the thickener W was sprinkled into the mixture and the resulting mass was stirred until all components were homogenously distributed.

Should the pH fail to range between 5.5 and 6.0 it is necessary to adjust the pH with sodium hydroxide solution or citric acid.

Example 6

Anti-Aging Hydrogel with Snow Algae Extract

TABLE 3

| Phase | Components | % w/w |
|---|---|---|
| W1 | water | ad 100 |
|  | glycerine | 2.5 |
|  | pentylene glycol | 5.0 |
| W2 | phenoxy ethanol | 0.80 |
| W3 | hydroxyethyl cellulose | 0.90 |
| A | snow algae extract | 2.0 |

The components as listed above in Table 3 were processed into an anti-aging hydrogel as described in the following:

Firstly, the components of the water phase W1 were blended, after which the phenoxy ethanol of phase W2 was dissolved in the water phase W1. Then the thickener W3 was sprinkled into the water phase and vigorously stirred, and the resulting solution was then hydrated for 2 hours under agitation. Then the snow algae extract was added and the blend stirred until having become homogenous.

Should the pH fail to range between 5.5 and 6.0 it is necessary to adjust the pH with sodium hydroxide solution or citric acid.

Example 7

Intensive Hair Mask with Snow Algae Extract

TABLE 4

| Phase | Components | % w/w |
|---|---|---|
| W1 | water | ad 100 |
|  | cetrimonium chloride | 0.70 |
|  | citric acid | 0.35 |
|  | hydroxyethyl cellulose | 0.20 |
| O1 | stearamido propyldimethyl amine | 1.00 |
|  | cetearyl alcoho | 5.00 |
|  | behentrimonium chloride | 2.00 |
|  | glycerol stearate | 1.50 |
|  | dicaprylyl ether | 0.60 |
| O2 | Bis($C_{13-15}$Alkoxy) PG Amodimethicone | 0.30 |
| P | perfume | q.s. |
| A | now algae extrac | 3.0 |

The components as listed above in Table 4 were processed into an intensive hair mask as described in the following:

The phase O1 components were blended and heated to 80° C.

The components of phase W1 were also blended and heated to 80° C. Then the components of phase W1 were added to phase O1 and homogenized for 2 minutes. The resulting homogenous mass was then cooled to 30 to 40° C. before the snow algae extract was added. After this, the perfume and phase O2 were added and the mass homogenized for 2 minutes, followed by cooling the homogenized mass to room temperature.

Should the pH fail to range between 3.5 and 4.5 it is necessary to adjust the pH with sodium hydroxide solution or citric acid.

In the following examples 8 and 9 use was made of normal human dermal fibroblasts (NHDF) isolated directly from the skin.

Example 8

Model with Naturally Aged Human Fibroblast Cells

Fibroblasts of passage 17 were incubated to confluency in the medium, after which the cells were incubated for 24 hours in a medium containing 1% by weight snow algae biomass of the present invention. The control samples were cells of passage 17 and 8 incubated solely in the medium. Of all formulations the expression of 64 aging marker genes were assayed by quantitive (real time) PCR.

TABLE 5

| Gene | rel. Expression P17/P8 | rel. Expression P17 treated/ P17 untreated |
|---|---|---|
| collagen 1 alpha 1 subunit | 0.46 | 1.63 |
| collagen 3 alpha 1 subunit | 0.58 | 3.4 |
| interleukin-6 | 0.53 | 4.89 |
| Klotho | 0.43 | 3.41 |

Example 9

Model with Prematurely Aged Human Fibroblast Cells

Fibroblasts of passage 8 were incubated in the medium containing 1% by weight snow algae biomass of the present invention, after which the cells were treated with $H_2O_2$ (600 μm during 2 hours). The control samples were cells of 8 with and without $H_2O_2$ treatment solely in the medium. Of all formulations the expression of 64 aging marker genes were assayed by quantitive (real time) PCR.

TABLE 6

| Gene | rel. Expression check $H_2O_2$ to check without $H_2O_2$ | rel. Expression $H_2O_2$ treated to $H_2O_2$ untreated |
|---|---|---|
| E2F-1 transcription factor | 1.56 | 0.52 |
| fatty acid binding protein 3 | 2.52 | 0.48 |
| insulin-like growth factor binding protein 7 | 1.42 | 0.45 |
| leptin-receptor | 4.47 | 0.64 |
| matrix metalloproteinase 1 | 5.30 | 0.53 |
| matrix metalloproteinase 3 | 10.24 | 0.60 |
| tissue factor pathway inhibitor 2 | 17.92 | 0.44 |
| thioredoxine | 1.72 | 0.53 |

Example 10

Dermatological Tests

A cream containing 3% by weight snow algae as the active ingredient was tested on the face in a half-side application. The test product was applied twice daily on 18 women and 2 men over a 3 week period. The placebo product was applied in each case to the other half of the face. All candidates spent the $2^{nd}$ week skiing. Before and after treatment the transepidermal water loss (TEWL) was determined and the wrinkles in the face assayed with the VisioFace® (Courage+Khazaka) apparatus. The results at the end of treatment showed that in the face half treated with the snow algae active ingredient the TEWL was lower by a significant 12%, whilst in the placebo side no significant change in the TEWL was evident. Analysis of the VisioFace® results showed a marked improvement in filling out the wrinkles after treatment with the snow algae cream, whilst, again, in the placebo side no significant change was evident.

The invention claimed is:

1. A method for delaying skin aging comprising applying to the skin of a subject in need thereof a product comprising an effective amount of lysed *Chlamydocapsa* sp CCryo 101-99 snow algae.

2. A method for protecting skin against the loss of the barrier function induced by environmental exposure, comprising applying to the skin of a subject in need thereof a cosmetic composition comprising an effective amount of a snow algae extract wherein the snow algae extract is homogenized *Chlamydocapsa* sp Ccryo 101-99 snow algae.

3. The method according to claim 1, wherein a Klotho anti-aging gene is activated.

4. The method according to claim 1, wherein genes for collagen production are activated.

5. The method according to claim 1, wherein gene expression of matrix metalloproteinases is reduced.

6. The method according to claim 2, wherein transepidermal water loss (TEWL) after environmental exposure to ultraviolet (UV) radiation, cold or dryness is reduced.

7. The method according to claim 2, wherein wrinkling of the skin induced by environmental exposure to ultraviolet radiation, cold or dryness is reduced.

8. The method according to claim 1, wherein the *Chlamydocapsa* sp Ccryo 101-99 snow algae has been induced to transform from the vegetative green phase into the stationary red phase prior to lysis.

9. The method according to claim 1, wherein the lysed *Chlamydocapsa* sp CCryo 101-99 snow algae comprises from 0.01% to 10% of the product.

10. The method according to claim 1, wherein the lysed *Chlamydocapsa* sp CCryo 101-99 snow algae is encapsulated in liposomes.

11. The method according to claim 1, wherein the lysed *Chlamydocapsa* sp CCryo 101-99 snow algae is encapsulated in nanoemulsions.

12. The method according to claim 11, wherein the nanoemulsions are dried to a powder on a matrix material.

13. The method according to claim 12, wherein the matrix material comprises isomalt and polyvinlpyrrolidone.

* * * * *